United States Patent

Koura et al.

(10) Patent No.: US 7,767,845 B2
(45) Date of Patent: Aug. 3, 2010

(54) PROCESS FOR PRODUCING OPTICALLY ACTIVE 2-HYDROXYBUTYRIC ESTER

(75) Inventors: Minoru Koura, Kawagoe (JP); Yukiyoshi Yamazaki, Higashimurayama (JP); Kimiyuki Shibuya, Tokorozawa (JP)

(73) Assignee: Kowa Co., Ltd., Nagoya-shi (JP)

( * ) Notice: Subject to any disclaimer, the term of this patent is extended or adjusted under 35 U.S.C. 154(b) by 147 days.

(21) Appl. No.: 11/994,877

(22) PCT Filed: Jul. 27, 2006

(86) PCT No.: PCT/JP2006/314882
§ 371 (c)(1),
(2), (4) Date: Jan. 7, 2008

(87) PCT Pub. No.: WO2007/013555
PCT Pub. Date: Feb. 1, 2007

(65) Prior Publication Data
US 2009/0209780 A1      Aug. 20, 2009

(30) Foreign Application Priority Data
Jul. 28, 2005   (JP)   ............... 2005-219163

(51) Int. Cl.
*C07C 69/66*   (2006.01)
(52) U.S. Cl. .................................................. 560/179
(58) Field of Classification Search .................. None
See application file for complete search history.

(56) References Cited

FOREIGN PATENT DOCUMENTS

| EP | 1661890 | 5/2006 |
|---|---|---|
| JP | 62 212329 | 9/1987 |
| JP | 4 36195 | 2/1992 |
| JP | 2004/533490 | 11/2004 |
| WO | WO2005/023777 | 3/2005 |

OTHER PUBLICATIONS

Tanikaga et al, Chemical Communications, Journal of the Chemical Society, Ready Nucleophilic Ring Opening of -Epoxy-sulphone, -sulfoxide and-ester with Grignard Reagents, 1986, pp. 836-837.*

Linstrumelle et al, Tetrahedron Letters, Copper-catalyzed Reactions of Allylic Grignard Reagents with Epoxides, 1978, 42, pp. 4069-4072.*

Kaoru Nakamura, et al., "Stereochemical Control on Yeast Reduction of alpha-Keto Esters. Reduction by Immobilized Bakers' Yeast in Hexane" J. Org. Chem. 1988, 53, pp. 2589-2593.

Reinaldo S. Compagnone, et al., "Chirospecific Synthesis of (+)-Pilocarpine", J. Org. Chem. 1986, 51, 1713-1719.

M. Novella Romanelli, et al., "Synthesis and Enantioselectivity of the Enantiomers of $PG_9$ and $SM_{21}$, New Potent Analgesic and Cognition-Enhancing Drugs" Chirality, 8, pp. 225-233 (1996).

Mark J. Burk, et al., "Rh-DuPHOS-Catalyzed Enantioselective Hydrogenation of Enol Esters. Application to the Synthesis of Highly Enantioenriched alpha-Hydroxy Esters and 1,2-Diols" J. Am. Chem. Soc., 1998, 120, pp. 4345-4353.

* cited by examiner

*Primary Examiner*—Paul A Zucker
(74) *Attorney, Agent, or Firm*—Oblon, Spivak, McClelland, Maier & Neustadt, L.L.P.

(57) ABSTRACT

A process for producing an optically active 2-hydroxybutyric ester represented by formula (1):

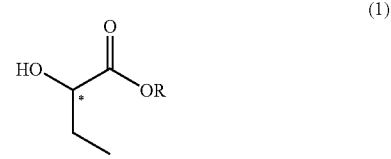

(1)

by reacting an optically active 2,3-epoxypropionic ester represented by formula (2):

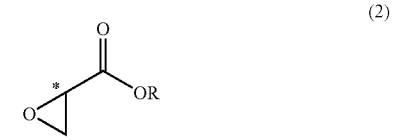

(2)

with a methyl Grignard reagent $CH_3MgX$ in the presence of a copper catalyst in an amount of 0.05 to 0.5 mol with respect to 1 mol of the 2,3-epoxypropionic ester.

10 Claims, No Drawings

PROCESS FOR PRODUCING OPTICALLY ACTIVE 2-HYDROXYBUTYRIC ESTER

TECHNICAL FIELD

The present invention relates to a process for producing an optically active 2-hydroxybutyric ester, which is a useful material for producing pharmaceuticals, pesticides, and industrial products.

BACKGROUND ART

Optically active 2-hydroxybutyric esters are compounds useful as a reagent or a starting material for producing pharmaceuticals, pesticides, and industrial products. For example, these esters serve as an important starting material for producing (R)-2-[3-[[N-(benzoxazol-2-yl)-N-3-(4-methoxyphenoxy) propyl]aminomethyl]phenoxy]butyric acid, which is a PPARα-selective activating agent and serves as a useful prophylactic and/or therapeutic agent for hyperlipemia, arteriosclerosis, diabetes, diabetes complications, inflammation, heart disease, etc., and is represented by the following formula (A):

[F1]

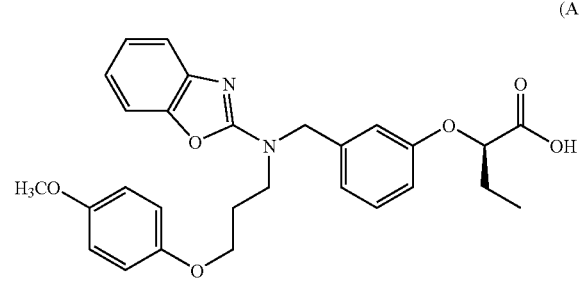

(A)

(Patent Document 1).

These optically active 2-hydroxybutyric esters are commercially available reagents (Aldrich), but are very expensive products. Hitherto, as shown in the following schemes, there have been known several processes for producing an optically active 2-hydroxycarboxylic ester derivative; for example, 1) a process for producing an optically active 2-hydroxybutyric ester through asymmetric reduction of a 2-ketobutyric ester by use of baker's yeast (Non-Patent Document 1); 2) a process for producing an optically active 2-hydroxybutyric ester from L-methionine as a starting material (Non-Patent Documents 2 and 3); 3) a process for producing an optically active 2-hydroxycarboxylic ester derivative through asymmetric reduction of an acrylic derivative (Non-Patent Document 4); and 4) a process for producing an optically active 2-hydroxycarboxylic derivative from an aldehyde starting material via an optically active cyanohydrin form (Patent Document 2).

[F2]

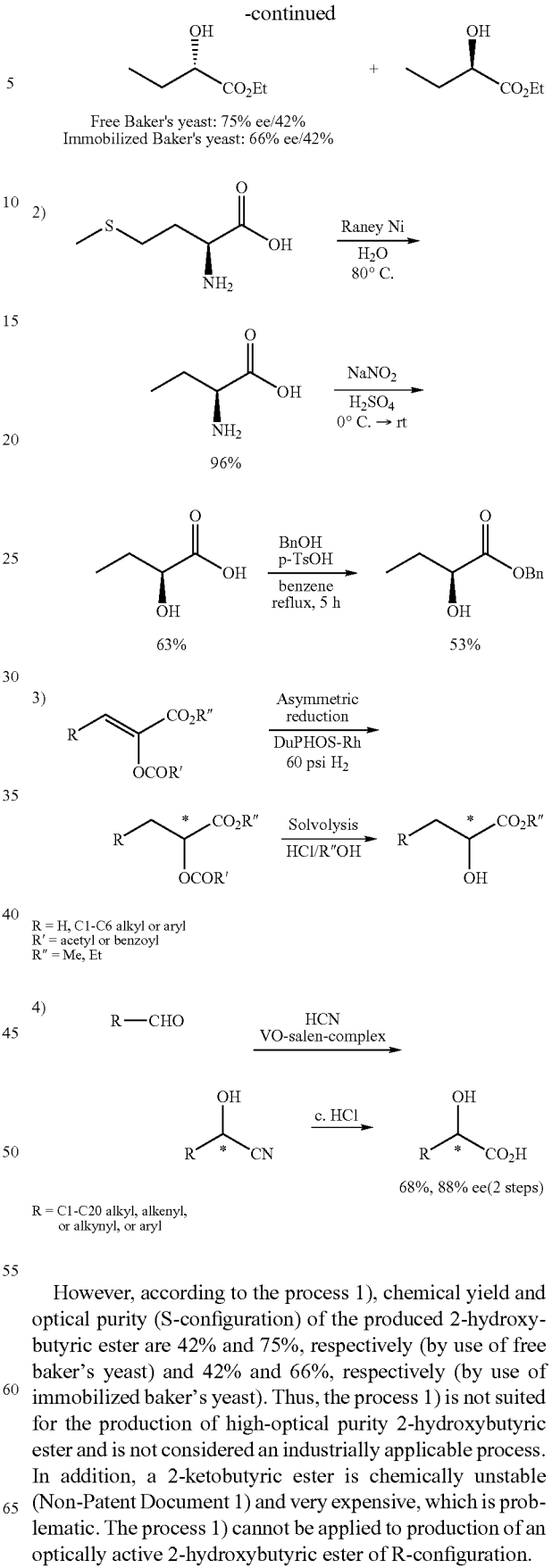

However, according to the process 1), chemical yield and optical purity (S-configuration) of the produced 2-hydroxybutyric ester are 42% and 75%, respectively (by use of free baker's yeast) and 42% and 66%, respectively (by use of immobilized baker's yeast). Thus, the process 1) is not suited for the production of high-optical purity 2-hydroxybutyric ester and is not considered an industrially applicable process. In addition, a 2-ketobutyric ester is chemically unstable (Non-Patent Document 1) and very expensive, which is problematic. The process 1) cannot be applied to production of an optically active 2-hydroxybutyric ester of R-configuration.

According to the process 2), a target optically active 2-hydroxybutyric ester can be produced from inexpensive L-methionine as a starting material. However, three steps are required for the target product, resulting in low overall yield, and a large amount of solvent is required for reaction and post treatment. Thus, the process 2) has problematically poor efficiency in terms of production conditions. In addition, since the process 2) includes a step of forming an unstable diazonium salt, reaction conditions are difficult to control, leading to variation in yield and optical purity of the target product. On a certain production scale, optical purity may drop considerably.

According to the process 3), the double bond of a 2-acyloxyacrylic ester derivative is asymmetrically reduced in the presence of an asymmetric catalyst, followed by solvolysis with an acid, whereby a target compound can be produced at high optical purity. However, the 2-acyloxyacrylic ester derivative serving as a starting material is produced through a complicated step, and the process includes preparation of an expensive asymmetric ligand and performing asymmetric reduction under pressurized hydrogen. Thus, the process 3) is not considered an industrially advantageous process.

According to the process 4), a 2-hydroxycarboxylic derivative is produced through two steps including asymmetric transformation of an aldehyde to a cyanohydrin and subsequent hydrolysis. However, preparation of an asymmetric catalyst requires a very complex step of designing an asymmetric ligand. Depending on a substituent of a reaction substrate, optical purity and chemical yield of the target compound are prone to vary, which is one disadvantage of the process.

Under such circumstances, demand has arisen for the development of a new process which realizes production of an optically active 2-hydroxybutyric ester at high yield and high optical purity.

Patent Document 1: International Patent Application Laid-Open WO2005/023777, pamphlet
Patent Document 2: Japanese Unexamined Patent Application Publication No. 2004-533490
Non-Patent Document 1: J. Org. Chem., 1988, 53, 2589-2593
Non-Patent Document 2: J. Org. Chem., 1986, 51, 1713-1719
Non-Patent Document 3: Chirality, 1996, 51, 225-233
Non-Patent Document 4: J. Am. Chem. Soc., 1998, 120, 4345-4353

DISCLOSURE OF THE INVENTION

Problems to be Solved by the Invention

An object of the present invention is to provide a process for producing an optically active 2-hydroxybutyric ester at high yield and high optical purity.

Means for Solving the Problems

In an attempt to attain the object, the present inventors have conducted extensive studies, and have chosen an optically active 2,3-epoxypropionic ester (2), which can be obtained in a large amount through an enzymatic method at relatively low cost. The inventors have found that reacting the ester (2) with a methyl Grignard reagent in the presence of a specific amount of a copper catalyst achieves regio-specific ring opening of the epoxy ring, whereby an optically active 2-hydroxybutyric ester (1) can be produced at high yield and high optical purity in a single step. The scheme is as follows:

[F3]

$$\text{(2)} \xrightarrow[\text{Copper catalyst}]{\text{CH}_3\text{MgX}} \text{(1)}$$

(wherein R represents a C1 to C6 alkyl group or a C7 or C8 aralkyl group; X represents a halogen atom; and * represents S- or R-absolute configuration).

Accordingly, the present invention is directed to a process for producing an optically active 2-hydroxybutyric ester represented by formula (1), characterized in that the process comprises reacting an optically active 2,3-epoxypropionic ester represented by formula (2) with a methyl Grignard reagent $CH_3MgX$ (wherein X represents a halogen atom) in the presence of a copper catalyst in an amount of 0.05 to 0.5 mol with respect to 1 mol of the 2,3-epoxypropionic ester.

EFFECTS OF THE INVENTION

According to the process of the present invention, an optically active 2-hydroxybutyric ester, which is a useful material for producing pharmaceuticals, pesticides, and industrial products, can be produced in a single step at high yield and high optical yield.

BEST MODES FOR CARRYING OUT THE INVENTION

Reaction carried out in the production process of the present invention will next be described in detail.

In formulas (2) and (1), R represents a C1 to C6 alkyl group or a C7 or C8 aralkyl group. Examples of preferred alkyl groups include methyl, ethyl, n-propyl, isopropyl, n-butyl, isobutyl, and t-butyl. Of these, n-butyl is more preferred. Examples of preferred aralkyl groups include benzyl and phenethyl.

In the methyl Grignard reagent $CH_3MgX$, the halogen atom X is preferably a chlorine atom, an iodine atom, or a bromine atom.

The methyl Grignard reagent is generally used in an amount of 1 to 20 mol with respect to 1 mol of optically active 2,3-epoxypropionic ester (2), preferably 1 to 3 mol.

The optically active 2,3-epoxypropionic esters represented by formula (2) are known compounds, and can be produced through a known method (e.g., a method disclosed in Japanese Patent Application Laid-Open (kokai) No. 5-276966).

In the above reaction, the aforementioned methyl Grignard reagent is reacted in the co-presence of a copper catalyst. Examples of the copper catalyst include copper(I) salts, specifically, copper(I) halides such as copper(I) iodide, copper(I) bromide, and copper(I) chloride; and copper(I) cyanide. Of these, copper(I) iodide is particularly preferred.

The copper catalyst is used in an amount of 0.05 to 0.5 mol with respect to 1 mol of optically active 2,3-epoxypropionic ester (2), preferably 0.075 to 0.15 mol.

When the amount is less than 0.05 mol, reaction does not sufficiently proceed, whereas when the amount is in excess of 0.5 mol, by-products increase, thereby lowering product yield.

The reaction may be performed in the presence or absence of solvent. Preferably, the reaction is performed in a solvent.

No particular limitation is imposed on the solvent employed in the reaction, and any solvent may be employed so long as it is not involved in the reaction. Examples of the solvent include ethers such as diethyl ether, tetrahydrofuran, 1,4- and 1,3-dioxane, t-butyl methyl ether, monoglyme, and diglyme; aromatic hydrocarbons such as benzene, toluene, xylene, mesitylene, chlorobenzene, and o-dichlorobenzene; aliphatic hydrocarbons such as n-hexane, cyclohexane, n-octane, and n-decane; and halohydrocarbons such as dichloromethane, dichloroethane, chloroform, and carbon tetrachloride. Of these, ethers such as diethyl ether, tetrahydrofuran, 1,4- and 1,3-dioxane, and t-butyl methyl ether are preferred, with diethyl ether and tetrahydrofuran being particularly preferred. These solvents may be used singly or in combination. No particular limitation is imposed on the amount of solvent employed.

The reaction is generally performed at −100 to 0° C., preferably −80 to −30° C. Generally, the reaction time is preferably 5 minutes to 5 hours, more preferably 10 minutes to 1 hour.

Preferably, the reaction is performed under argon or nitrogen.

No particular limitation is imposed on the mode of reaction. Examples of the reaction mode include Method 1) including suspending a copper catalyst in a solvent such as diethyl ether to thereby form a suspension, dissolving a methyl Grignard reagent in the aforementioned solvent to form a solution, adding the solution to the suspension so as to perform metal exchange, and continuously adding a solution of an optically active 2,3-epoxypropionic ester (2) dissolved in a solvent thereto; Method 2) including suspending a copper catalyst in a solvent such as diethyl ether to thereby form a suspension, adding a solution of an optically active 2,3-epoxypropionic ester (2) dissolved in the aforementioned solvent to the suspension, and continuously adding a solution of a methyl Grignard reagent dissolved in a solvent thereto; and Method 3) including adding a copper catalyst to a solution of an optically active 2,3-epoxypropionic ester (2) dissolved in a solvent such as diethyl ether, and continuously adding a solution of a methyl Grignard reagent dissolved in a solvent to the mixture. Of these, from the viewpoint of production of a target compound having high yield and high optical purity, preferred is a method including suspending a copper catalyst in a solvent such as diethyl ether to thereby form a suspension, reacting a methyl Grignard reagent with the suspension so as to perform metal exchange, and reacting the mixture with an optically active 2,3-epoxypropionic ester (2). In a particularly preferred mode, copper(I) iodide is used in an amount of 0.075 to 0.15 mol with respect to 1 mol of an optically active 2,3-epoxypropionic ester (2), and the mixture is reacted with a methyl Grignard reagent so as to perform metal change, followed by reacting the resultant mixture with the optically active 2,3-epoxypropionic ester (2) at −80 to −30° C. for 10 minutes to 1 hour.

After completion of reaction, the reaction mixture is subjected to hydrolysis with water, an aqueous ammonium chloride solution, or a mineral acid such as hydrochloric acid or sulfuric acid, preferably with an aqueous ammonium chloride solution, whereby a target compound (1) can be produced.

In the present invention, if required, a target product of each reaction may be isolated through any purification method generally employed in organic synthetic chemistry; e.g., filtration, washing, drying, re-crystallization, chromatographic processes, or distillation.

EXAMPLES

The present invention will next be described in more detail by way of examples.

Example 1

Synthesis of n-butyl(S)-2-hydroxybutyrate

Under argon, copper(I) iodide (594 mg) was suspended in anhydrous diethyl ether (20.0 mL). A solution of methylmagnesium bromide in anhydrous tetrahydrofuran (60.2 mL, M) was added dropwise to the suspension at −15° C. or lower, and the mixture was allowed to react at the same temperature for 20 minutes. After completion of reaction, a solution (8.0 mL) of n-butyl(S)-(−)-2,3-epoxypropionate (3.0 g, 97.3% ee) (product of Osaka Organic Chemical Industry Co., Ltd.) in anhydrous diethyl ether was added dropwise to the reaction mixture at −78° C., and the resultant mixture was allowed to react for 15 minutes at the same temperature. After completion of reaction, an aqueous saturated ammonium chloride solution (50.0 mL) was added to the reaction mixture, followed by filtration by means of a Celite. The filtrate was extracted twice with diethyl ether (50 mL×2), and the organic layer was washed with saturated brine (40 mL). The washed organic layer was dried over sodium sulfate anhydrate and concentrated under reduced pressure. The residue was subjected to silica gel column chromatography including elution with methylene chloride/diethyl ether=5/1, to thereby yield 3.37 g of colorless oil (yield 99.0%). Since the compound was also able to be purified through distillation under reduced pressure, another aliquot of the residue obtained through the same procedure was distillated under reduced pressure, to thereby yield 2.73 g of colorless oil (yield 81.8%).

IR (ATR); 3483, 2962, 2935, 2876, 1731, 1463, 1381, 1244, 1206, 1132, 1059, 994, 841, 738, 678 cm$^{-1}$ $^1$HNMR (400 MHz, CDCl$_3$)δ; 0.93(t, J=7.8 Hz, 3H), 0.94 (t, J=7.8 Hz, 3H), 1.37(qt, J=7.5, 7.4 Hz, 2H), 1.59-1.72(m, 3H), 1.77-1.85(m, 1H), 2.71(d, J=5.6 Hz, 1H), 4.11-4.23(m, 3H).

b.p.; 66 to 68° C. (2 mmHg).

EI-MS m/z; 161 (M$^+$+H).

Elemental analysis (as C$_8$H$_{1603}$) calcd.: C, 59.97; H, 10.07. found: C, 60.03; H, 10.09.

Optical Purity:

As shown in the following scheme, optical purity was determined through HPLC analysis with derivatization to a 4-nitrobenzoic ester.

[F4]

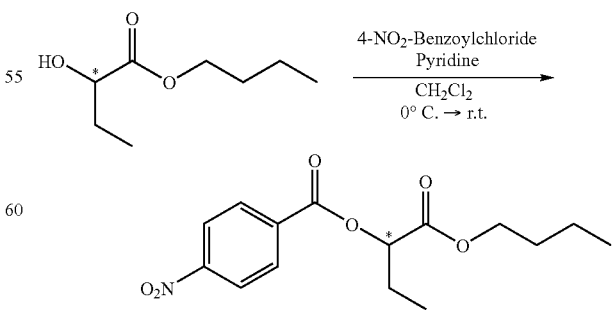

n-Butyl(S)-2-hydroxybutyrate (30 mg) was dissolved in a mixture of methylene chloride (1 mL) and pyridine (0.02 mL). 4-Nitrobenzoyl chloride (35 mg) was added at 0° C. to the mixture, followed by stirring at 0° C. for 10 minutes and at room temperature for 5 hours. Water (5 mL) was added to the reaction mixture with stirring for 5 minutes, and chloroform mL) was added thereto. The organic layer was washed sequentially with 4N hydrochloric acid, water, aqueous saturated sodium hydrogen carbonate solution, and saturated brine. The washed product was dried over sodium sulfate anhydrate and concentrated under reduced pressure. The residue was purified through collective thin-layer chromatography (n-hexane/chloroform=1/1), to thereby yield 31 mg of colorless oil (54%, optical purity: 96.5% ee).

Measurement Conditions (HPLC)
Column: CHIRALPAK AD
Column temperature: 35° C.
Solvent: n-hexane/ethanol=60/40
Flow rate: 1 mL/min
Retention time: 5.96 min (R form: 4.43 min)

Examples 2 to 6 and Comparative Examples 1 to 3

Reaction was performed in a manner similar to Example 1 and under the conditions shown in Table 1. Isolation yields are also given in Table 1. Notably, in all cases, n-butyl (S)-(−)-2,3-epoxypropionate was used in an amount of 200 mg and anhydrous diethyl ether was used as a reaction solvent.

TABLE 1

| Entry | Cu catalyst | eq. | Reaction conditions | Yield |
|---|---|---|---|---|
| Ex. 2 | CuI | 0.075 | −78° C., 3.5 h | 184 mg (83%) |
| Ex. 3 | CuI | 0.15 | −20° C., 15 min | 143 mg (64%) |
| Ex. 4 | CuI | 0.15 | −78° C., 15 min | 220 mg (99%) |
| Ex. 5 | CuCl | 0.15 | −78° C., 15 min | 177 mg (79%) |
| Ex. 6 | CuBr | 0.15 | −78° C., 15 min | 169 mg (76%) |
| Comp. Ex. 1 | CuI | 0 | −78° C., 2.5 h | — |
| Comp. Ex. 2 | CuI | 0.75 | −78° C., 15 min | 92 mg (41%) |
| Comp. Ex. 3 | CuI | 1.5 | −78° C., 2.5 h | — |

—: Difficulty in product isolation and purification due to complicated product system.

As is clear from Table 1, the highest yield was attained under the conditions: −78° C., 15 minutes, and use of catalyst (copper(I) iodide) in an amount of 0.15 mol equivalent. When an excessive amount of catalyst was employed, yield decreased, and a complicated product system was formed. When no catalyst was used, a complicated product system including an unreacted substance was formed; i.e., no target product was obtained.

The invention claimed is:

1. A process for producing an optically active 2-hydroxybutyric ester represented by formula (1):

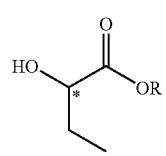

wherein R represents a C1 to C6 alkyl group or a C7 or C8 aralkyl group; and * represents S- or R-absolute configuration, wherein the process comprises reacting an optically active 2,3-epoxypropionic ester represented by formula (2):

wherein R and * have the same meanings as defined above with a methyl Grignard reagent $CH_3MgX$, wherein X represents a halogen atom, in the presence of a copper catalyst in an amount of 0.05 to 0.5 mol with respect to 1 mol of the 2,3-epoxypropionic ester.

2. The process as described in claim 1, wherein the copper catalyst is a copper(I) halide.

3. The process as described in claim 2, wherein the copper (I) halide is copper(I) iodide.

4. The process as described in claim 1, wherein the copper catalyst is used in an amount of 0.075 to 0.15 mol with respect to 1 mol of 2,3-epoxypropionic ester.

5. The process as described in claim 1, wherein reaction is performed at −80 to −30° C. for 10 minutes to 1 hour.

6. The process as described in claim 2, wherein the copper catalyst is used in an amount of 0.075 to 0.15 mol with respect to 1 mol of 2,3- epoxypropionic ester.

7. The process as described in claim 3, wherein the copper catalyst is used in an amount of 0.075 to 0.15 mol with respect to 1 mol of 2,3-epoxypropionic ester.

8. The process as described in claim 2, wherein reaction is performed at −80 to −30° C. for 10 minutes to 1 hour.

9. The process as described in claim 3, wherein reaction is performed at −80 to −30° C. for 10 minutes to 1 hour.

10. The process as described in claim 4, wherein reaction is performed at −80 to −30° C. for 10 minutes to 1 hour.

* * * * *